United States Patent [19]

Gelfand et al.

[11] Patent Number: 4,830,962
[45] Date of Patent: May 16, 1989

[54] RECOMBINANT DIPHTHERIA TOXIN FRAGMENTS

[75] Inventors: David H. Gelfand, Oakland; Lawrence I. Greenfield, Albany; Frances C. Lawyer, Oakland, all of Calif.

[73] Assignee: Cetus Corporation, Emeryville, Calif.

[21] Appl. No.: 578,122

[22] Filed: Feb. 9, 1984

[51] Int. Cl.$^4$ .................... C12P 21/00; C12N 15/00; C12N 1/20
[52] U.S. Cl. .................... 435/68; 435/172.3; 435/320; 435/252.33; 435/252.31; 435/252.34; 536/27
[58] Field of Search ............ 435/68, 172.3, 317; 935/6, 22, 66; 536/27

[56] References Cited

U.S. PATENT DOCUMENTS 4,237,224  12/1980  Cohen et al. .................... 435/68

OTHER PUBLICATIONS

Buck et al 1981 "Identification of Deoxyribonucleic Acid Restriction Fragments of B-Converting Corynebacteriophages . . ." *J. Bact* v148(1) 153–62.
Matteucci et al 1981 "Synthesis of Deoxyoligonucleotides on a Polymer Support" *J Am Chem Soc* v103 3185–91.
Kaczorek et al "Nucleotide Sequence and Expression of the Diphtheria tox 228 Gene in *E. coli*" *Science* v 221 pp. 855–858.
Leong et al 1983 "Cloned Diphtheria Toxin Fragment A is Expressed from the tox Promoter . . ." *J. Biol Chem* 258 pp. 15016–15020.
DeLange et al 1979(a) "The Amino Acid Sequence of Fragment A . . . I. The Tryptic Peptides from the Maleylated Protein" *J. Biol Chem* 254 pp. 5827–5831.
Drazin et al 1979 "The Amino Acid Sequence of Fragment A . . . II The Cyanogen Bromide Peptides" *J Biol Chem* v254 5832–37.
DeLange et al 1979(b) "The Amino Acid Sequence of Fragment A . . . III The Chymotryptic Peptides . . . " *J. Biol Chem* v254 5838–42.
Maniatis et al 1982 *Molecular Cloning: A Laboratory Manual* Cold Spring Harbor Labs. pp. 392, 393, 405 & 406.
Yamaizumi et al 1978 *Cell* v15 245–50.
Kagan et al 1981 *Proc Natl Acad Sci* v78 4950–54.
Donovan et al 1981 *Proc Natl Acad Sci* v78 172–176.
Lambotte et al 1980 *J. Cell Biol* v87 837–40.
Rath et al 1983 *Nucl. Acids Res* v11 6589–95.
Kayser et al 1981 *Bioch and Biophys Res. Comm* v99 358–63.
Leong et al 1983 *Science* v220 515–18.
Greenfield et al 1983 *Proc Natl Acad Sci* v80 6853–57.
Tweten et al 1983 *J. Bact.* v156 680–85.
Maniatis et al 1982 *Molecular Cloning* Cold Spring Harbor Lab. pp. 412–413.

*Primary Examiner*—Blondel Hazel
*Attorney, Agent, or Firm*—Albert P. Halluin; Elliott L. Fineman; Thomas E. Ciotti

[57] ABSTRACT

Recombinant vectors which are effective in expressing DNA sequences encoding specific fragments of diphtheria toxins at high levels in recombinant host cells are disclosed. Both a fragment consisting of the enzymatically active A chain of diphtheria toxin and a fragment consisting of both the A portion and a B portion partial sequence are constructed by use of this recombinant vector.

24 Claims, 6 Drawing Sheets

FIG. 1-1

(rotated sideways - DNA/protein sequence figure)

```
                          Msp I
                          CCGGGCGTTGCG TATCCAGTGGCTACACTCAGGTTGTAATGA
TAAAACTCATTGAGGAGTAGGTCCCGATT GGTTTTGCTAGTGAAGCTTAGCTTT CCCCATGTACCAATCTATCAAAAAGGGC
TAGCTTTACCTAATTATTTATGAGTCCTG GTAAGGGGATACGTTGTGAGAGAAACTG TTTGCGTCAATCTTAATAGGGGCGTACTG
                              TerValLeu  ValArgGlyTyrValSerArgLysLeu  PheAlaSerIleLeuIleGlyAlaLeuLeu
                                -31              -21                            -11
GGCGCTGATGATGTTGTTGATTCTTCTAAA TCTTTTGTGATGGAAAACTTTTCTTCGTAC CACGGGACTAAACCTGGTTATGTAGATTCC
GlyAlaAspAspValValAspSerSerLys SerPheValMetGluAsnPheSerSerTyr HisGlyThrLysProGlyTyrValAspSer
            1                           10                              20
GGTACACAAGGAAATTATGACGATGATTGG AAAGGGTTTATAGTACCGACAATAAATAC GACGCTGCGGGATACTCTGTAGATAATGAA
GlyThrGlnGlyAsnTyrAspAspAspTrp LysGlyPheTyrSerThrAspAsnLysTyr AspAlaAlaGlyTyrSerValAspAsnGlu
            30                           50                              60
GTCAAAGTGACGTATCCAGGACTGACGAAG GTTCTCGCCACTAAAAGTGGATAATGCCGA ACTATTAAGAAAGAGTTAGGTTTAAGTCTC
ValLysValThrTyrProGlyLeuThrLys ValLeuAlaLeuLysValAspAsnAlaGlu ThrIleLysLysGluLeuGlyLeuSerLeu
            90                           100                             110
GAAGAGTTATCAAAAGGTTCGGTGATGGT GCTTCGCGTGTAGTGCTCAGCCTTCCCTTC GCTGAGGGAGTTCTAGCGTTGAATATATT
GluGluPheIleLysArgPheGlyAspGly AlaSerArgValValLeuSerLeuProPhe AlaGluGlySerSerSerValGluTyrIle
            130                          140                             150
GTAGAACTTGAGATTAATTTTGAAACCCGT GCAAAACTGGCCAAGATGCCGATGTATGAG TATATGGCTCAAGCCTGTGCAGGAAATCGT
ValGluLeuGluIleAsnPheGluThrArg GlyLysArgPheGluThrGlu TyrMetAlaGlnAlaCysAlaGlyAsnArg
            170                          180                             190
```

```
                              Mbo I
                              TTGGGATGATGTACCTCGATCTGAGAGCCAT
ATTGATTCAGAGCACCTTATAATTAGGA
GGGATAGGGCCCACTTCAGCCCATGCA
GlyIleGlyAlaProProSerAlaHisAla
              -1
ATTCAAAAGGTATACAAAGCCAAAATCT
IleGlnLysGlyIleGlnLysProLysSer
              40
AACCCGCTCTCTGAAAAGCTGGAGGCTG
AsnProLeuSerGlyLysAlaGlyGlyVal
              80
ACTGAACCGTTGATGGAGCAAGTCGAACG
ThrGluProLeuMetGluGlnValGlyThr
              120
AATAACTGGGAACAGGCGAAAGCCTTAAGC
AsnAsnTrpGluGlnAlaLysAlaLeuSer
              160
                              Mbo I
GTCAGGCGATCACTAGTAGCTCATTGTCA
ValArgArgSerValGlySerLeuSer
              200
```

FIG. 1-2

FIG_2.

RECOMBINANT DIPHTHERIA TOXIN FRAGMENTS

DESCRIPTION

1. Technical Field

The invention herein relates to the production of toxin fragments using recombinant technology. More specifically, the invention relates to producing diphtheria toxin A fragment and a diphtheria toxin A-partial B fragment using recombinant means.

2. Background Art

Diphtheria toxin (DT) is a representative example of a number of naturally occurring toxins which are composed of an enzymatically active, cytotoxic "A" amino acid sequence and a "B" sequence which is presumed responsible both for attaching the A sequence to a target cell to be killed and to aid in the translocation of the A fragment into the cytoplasm. Diphtheria toxin A fragment is capable of cytotoxicity, apparently, because it catalyzes the transfer of ADP-ribose from NAD to elongation factor-2 (EF-2) which thereby blocks protein synthesis and causes cell death. *Pseudomonas aeruginosa* exotoxin A also shows the same basis for cytotoxic activity; other toxins, such as cholera toxin, catalyze the transfer of ADP-ribose to the adenylate cyclase complex. Thus, the enzymatic activity of the A fragment is similar to that associated with other naturally occurring toxins.

DT is secreted from *Corynebacterium diphtheriae* as a single polypeptide chain containing 535 residues, of which the amino terminal, approximately 193 residue sequence, is considered the A fragment, and the carboxyterminal, approximately 342 residue sequence, is considered the B component. The amino acid sequence of the naturally occurring diphtheria toxin, deduced from the coding sequence, is included in FIG. 1. In this naturally occurring protein, the A chain is considered to end roughly after the arginine at position 193, and the B chain to pick up with the serine at position 194. It is believed that cleavage after one of the Arg residues at positions 190, 192 or 193 (trypsin is capable of thus cleaving in vitro) is required for intoxication of cells. This alteration is believed to be followed by breakage of the disulfide bond between cysteine at position 186 and cysteine at position 201 so as completely to free the A fragment from B fragment. Once released inside the cell, it is known that a single molecule of fragment A can be lethal for an individual cell (Yamaizumi, M., et al, *Cell* (1978) 15:245). This is believed to be attributable to the catalytic nature of the cytotoxic effect.

It is believed that the hydrophobic sequence of approximately 32 amino acids in the vicinity of residue 350 is responsible for the translocation properties of B chain. A "cross reacting mutant" secretes "CRM 45," a modified form of DT which contains approximately half of the B portion at the N-terminal end. CRM 45 is capable of insertion into artificial lipid bilayers under appropriate in vitro conditions to form ion conductive channels (Kagan, B. L., et al, *Proc Natl Acad Sci* (USA) (1981) 4950; Donovan, J. J., et al, *Ibid* (1981) 78:172; Kayser, B. et al, *Biochem Biophys Res Commun* (1981) 99:358). Further, the 25 amino acid region referred to above was earlier identified by Lambott, P., et al, *J Cell Biol* (1980) 8:837, as especially hydrophobic and to resemble transverse lipid-associating domains found in intrinsic membrane proteins.

FIG. 1 also shows that the DT protein contains a leader sequence responsible for secretion from Corynebacter, presumably initiated at the GTG codon at position -25. The invention utilizes portions of the gene cleavable at MspI (fragment 2) and MboI (fragment 1); these portions contain at least part of the control sequences native to DT, and will be deleted in most of the vectors of the invention.

The gene sequence has been disclosed by Ratti, G., et al, *Nucleic Acids Res* (1983) 11:6589; by Leong, D., et al, *Science* (1983) 220:515 and by Greenfield, L., et al, *Proc Natl Acad Sci* (USA)(1983) 80:6853–6857. Expression *E. coli* of Mbo (fragment 1) and Msp (fragment 2) has been detected at low levels in *E. coli* transformed with pBR322 derived plasmids containing these inserted sequences. (Tweten, R. K., et al, *J Bacteriol* (1983) 156:680.)

The present invention provides a means to produce efficiently and controllably precise fragments of the toxin molecule. Such fragments are useful, for example, as intermediates in the construction of immunotoxin conjugates for therapy. In such approaches, the toxin fragments are linked to specific antibodies raised against desired target cells, and such specificity can be used to focus the cytotoxicity of the toxin on undesirable cells such as tumors. Further, the method of the invention provides a means for significant production of desired fragments to permit systematic study of the molecular basis for the properties of toxins. Since the sequence is manipulated at the genetic level, specific desired alterations in structure can also be made.

Previous methods of preparation result in fragments of unpredetermined sequence, and/or are costly and inefficient. This invention, by providing effective expression vectors capable of high levels of expression in suitable hosts, is capable of insuring the production of the desired sequences in high levels.

DISCLOSURE OF THE INVENTION

The invention provides a means to prepare useful quantities of diphtheria toxin fragments of predetermined sequence which are useful as intermediates in construction of conjugate toxins and as means to study toxin characteristics. The method of the invention takes advantage of recombinant techniques.

Hence, in one aspect, the invention relates to expression vectors which are constructed so as to contain the desired coding sequence for a predetermined DT fragment and which are capable of effecting efficient expression of the sequences. The invention includes vectors for the expression of DT-A fragment, and a DT-A-B' fragment (a cytotoxic peptide which contains an intracellular cleavage/extracellularly stable site as well as a translocation assisting sequence). Preferred vectors utilize DNA control sequences which are not native to the coding sequences, but are particularly compatible with the host. In a desired construction, all native control sequences and leader encoding sequences are absent.

In other aspects, the invention relates to cells transformed with the expression vectors of the invention, and to cultures thereof. The invention in one embodiment further relates to a method for preparing DT-A fragment and DT-A-B' fragment using the vectors and cells of the invention, and to the DT-A and DT-A-B' fragments prepared thereby. Such production can be caused to occur at levels greater than 5 μg per ml of cell culture.

BRIEF DESCRIPTION OF THE DRAWINGS

FIG. 1 shows the nucleotide sequence of the DT gene as isolated between MspI restriction sites. The deduced amino acid sequence is also shown.

FIG. 6 shows the results of SDS-PAGE using extracts of cells transformed with the vectors of the invention.

MODES FOR CARRYING OUT THE INVENTION

A. Definitions

"DT-A fragment" (diphtheria toxin-A fragment) refers to an approximately 193 residue amino acid sequence which is capable of ADP-ribosylation of EF-2, and which corresponds substantially and functionally to the sequence in FIG. 1 between amino acid 1 and amino acid 192 or 193.

"DT-B fragment" is an approximately 343 residue amino acid sequence which corresponds substantially and functionally to the sequence approximately between amino acids 193 and 535 in FIG. 1.

"DT-A-B' fragment" is an approximately 384 residue amino acid sequence which is capable of ADP-ribosylation of EF-2, which contains both a translocation sequence and an intracellular cleavage site within an extracellularly stable domain, and which corresponds substantially and functionally to the sequence shown in FIG. 1 between amino acid 1 and amino acid 384.

Where sequences herein are described as "corresponding substantially and functionally to" the sequence in FIG. 1 or to a particular portion thereof, this correspondence is to the specific sequence there shown, plus modifications which do not destroy the functionality of the sequence. Thus, the biological properties such as enzymatic activity, translocation properties, etc., must be preserved with respect to any modifications. The length of the sequence, moreover, is only approximate and is intended to be within 10 amino acids of the stated terminus at either the N or C end; further, alterations in the precise sequence (such as replacement of, deletion of, or addition of one or several amino acids) which do not destroy functionality of the given sequences are included within the definition. Thus, in particular, a sequence corresponding to the first 384 amino acids of the toxin but having an additional cysteine residue at position 385 falls within the definition.

"Msp fragment" (fragment 2) refers to an approximately 1454 bp segment which contains all of the A portion and part of the B portion—i.e., a DT-A-B' fragment along with at least part of native promoter, ribosome binding site and secretory leader sequence as shown in FIG. 1. "Msp terminator" refers to a nucleotide sequence (synthetically derived herein) which encodes one additional amino acid past the Msp cleavage point plus a stop codon. The resultant (Msp+Msp terminator) encodes a "DT-A-B' fragment."

"Mbo fragment" (fragment 1) refers to an approximately 831 bp resultant of an Mbo digest of the DT gene. It contains the coding sequence of amino acids 1-193 (the A chain) and leader and at least partial native control sequences (see FIG. 1). "Mbo terminator" refers to a nucleotide sequence (synthetically derived herein) which encodes an additional six amino acids past the Mbo cleavage plus a stop codon. The resultant (Mbo+Mbo terminator) encodes a "DT-A fragment."

"Native" promoter, ribosome binding site, or control sequences refer to those which are normally found in association with, and operably linked to, the DT coding sequence. "Leader" sequence refers to that portion of the DNA which encodes the native pre-sequence, responsible for secretion of the mature protein.

"Operably inked" when used in describing DNA sequences refers to juxtaposition in such a way that the functionality of the sequences is preserved. Thus, a coding sequence "operably linked" to a promoter is positioned in such a way that the promoter is capable of effecting the expression of the coding sequence.

"Control" sequence refers to those sequences which control initiation of transcription and translation. In procaryotic systems, control sequences comprise promoter or promoter/operator and nucleotides encoding a ribosome binding site.

"Recombinant host cells" refers to cells which have been transformed with DNA sequences which have been constructed by recombinant techniques. Such reference includes both the cells as separated, for example by filtration or as a centrifugation pellet, and to cultures of these cells. Indeed, "cells" and "cell cultures," where the context so permits, are often used interchangeably herein.

B. Vectors and Host Cells

The specific embodiments described hereinbelow set forth procedures for constructing vectors compatible with procaryotes, and for transformation of such vectors into these host cells. E. coli K12 strain, MM294 and a lambda lysogen of E. coli strain MC1000, are described in particular. However, other microbial strains may also be used, such as bacilli, for example Bacillus subtilis, various species of Pseudomonas, or other bacterial strains. In such procaryotic systems, plasmid vectors which contain replication sites and control sequences derived from a species compatible with the host are used. For example, E. coli is typically transformed using derivatives of pBR322, a plasmid derived from an E. coli species by Bolivar, et al, Gene (1977) 2:95. pBR322 contains genes for ampicillin and tetracycline resistance, and thus provides markers which can be either retained or destroyed in constructing the desired vector. Commonly used procaryotic control sequences which are defined herein to include transcription initiation, optionally operator, and ribosome binding site sequences, include such commonly used promoters as the betalactamase (penicillinase) and lactose (lac) promoter systems (Chang, et al, Nature (1977) 198:1056 and the tryptophan (trp) promoter system (Goeddel, et al, Nucleic Acids Res (1980) 8:4057 and the lambda derived P$_L$ promoter and N-gene ribosome binding site (Shimatake, et al, Nature (1981) 292:128. However, any available promoter system compatible with procaryotes can be used.

In addition to bacteria, eucaryotic microbes, such as yeast, may also be used. Saccharomyces cerevisiae, Baker's yeast, is most commonly used although a number of other strains are commonly available. A number of plasmid vectors suitable for yeast expression are also known (see, for example, Stinchcomb, et al, *Nature* (1979) 282:39, and Tschempe, et al, *Gene* (1980) 10:157). Promoters for yeast vectors include promoters for the synthesis of glycolytic enzymes (Hess, et al, *J Adv Enzyme Reg* (1968) 7:149; Holland, et al, *Biochemistry* (1978) 17:4900). Any vector containing a yeast compatible promoter, origin of replication and other control sequences is suitable.

More recently, it has been found possible to express genes encoding polypeptides in eucaryotic host cell cultures derived from multicellular organisms. See, for example, *Tissue Cultures*, Academic Press, Cruz and Patterson, editors (1973). Useful host cell lines include VERO and HeLa cells, and Chinese hamster ovary (CHO) cells. Expression vectors for such cells ordinarily include promoters compatible with mammalian cells such as, for example, the commonly used early and late promoters from Simian Virus 40 (SV 40) (Fiers, et al, *Nature* (1978) 273:113).

Depending on the host cell used, transformation is done using the calcium treatment employing calcium chloride, as described by Cohen, S. N., *Proc Natl Acad Sci* (USA) (1972) 69:2110, for procaryotes or other cells which contain substantial cell wall barriers, or, for mammalian cells without such cell walls, the calcium phosphate precipitation method of Graham and van der Eb, *Virology* (1978) 52:546.

The successful expression attained by the invention depends upon correct utilization of the suitable control sequences to regulate expression of the desired toxin fragment. Therefore, whatever the host, control sequences compatible with and suitable for that host are positioned in operably with respect to the coding sequence, using a properly placed "start" codon at the 5' end of the desired sequence. Any "native" control sequences are eliminated. Since in the expression vectors of the present invention the leader portion of the toxin is not desired, DNA encoding such amino acids is also deleted. Thus, the vectors of the invention place the coding sequence for the desired DT-A and DT-A-B' fragments, immediately preceded by an ATG start codon directly downstream from control systems chosen to be compatible with the particular host.

It is also important, in obtaining good production of the desired fragments, to regulate the "time" of production so as to minimize any lethal effect on the host cell. Most typically, this is done by delaying expression of the DT sequences until substantial growth has occurred. Accordingly, it is desirable to utilize control sequences which are subject to environmental conditions. By maintaining conditions that repress expression during growth phase, and then converting to conditions which permit expression at the desired time, the negative aspects of any potentially lethal effect can be minimized.

In two particularly preferred approaches, these regulatable control sequences are compatible with procaryotic hosts. The trp promoter is a regulatable promoter where expression of the operably linked sequence can be controlled by the level of tryptophan in the medium. By maintaining high tryptophan levels during growth, expression is repressed. Depletion or competitive inhibition of tryptophan turns on the promoter and permits expression.

Still more preferred is the $P_L$ promoter derived from λ phage. This promoter is regulated by a protein which can be temperature sensitive. (There are mutant forms of the wild type repressor, e.g., $CI_{857}$ which have this characteristic known in the art.) When used in a host which is able to synthesize this mutant form of repressor (such as *E. coli* K12 strain MC1000 lysogenic for the λ phage $N_7N_{53}CI_{857}SusP_{80}$), the $P_L$ promoter will be switched on when the temperature is raised because the higher temperature inactivates the mutant CI repressor. Thus, the host cells can be grown at low temperature without production of the foreign protein. The temperature is then raised when growth has been attained and DT production is desired.

Another, not necessarily independent approach, involves use of a plasmid which has temperature sensitive copy number control, so that if the cells are grown at low temperatures, coding sequences contained in the plasmid are replicated at low levels; at higher temperatures, the number of such copies is inceased. The amount of protein produced is thus indirectly managed by regulating the number of available copies of its coding sequence.

If both approaches are used concommitantly, an increase in temperature results in both an increase in copy number and a de-repression of promoter leading to substantial synthesis of otherwise repressed gene products.

C. Methods Employed

Isolation of the DNA fragments comprising the desired coding sequences is described in detail herein below. Vector construction employs ligation and restriction techniques known in the art. The quantity of DNA available can be increased by cloning the desired fragments, i.e., inserting into a suitable cloning vehicle, such as pBR322, transforming and replicating in *E. coli,* and, optionally further enhancing through chloramphenicol amplification or by phage replication. The desired fragments can then be removed from the cloning vectors or phage and ligated to suitable promoters compatible with the host intended to be employed in the expression of the gene. Such hosts are then transformed with these expression vectors and cultured under conditions which favor stabilization of the plasmid and the safe production of the desired toxin fragments. Such conditions might include repression of the controlling promoter until most of log phase has been completed, and then altering conditions so as to favor the synthesis of the peptide.

When the peptide has been synthesized, the cells are lysed, and the desired fragment recovered from the lysate. It is also within the scope of the invention, although not a preferred embodiment, to retain the portion of the coding sequence for the native protein which contains the leader sequence associated with native DT. In such case, the peptide may be secreted into the medium or into the periplasmic space, depending on the host.

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g, New England Biolabs, Product Catalog. In general, about 1 µg of plasmid or DNA sequence is cleaved by one unit of enzyme in about 20 µl of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform followed by ether extraction and the nucleic acid recovered from aqueous fractions by precipitation with ethanol followed by running over a Sephadex G-50 spin column. If desired, size separation of the cleaved fragments may be performed by polyacrylamide gel electrophoresis using standard techniques. A general description of size separations is found in *Methods in Enzymology* (1980) 65:499-560.

Restriction cleaved fragments may be blunt ended by treating with the large fragment of *E. coli* DNA polymerase I (Klenow) in the presence of the four nucleotide triphosphates (dNTPs) using incubation times of about 15 to 25 min at 20° to 25° C. in 50 mM Tris pH 7.6, 50 mM NaCl, 6 mM $MgCl_2$, 6 mM DTT and 0.1 mM dNTPs. The Klenow fragment fills in at 5' sticky ends but chews back single strands, even though the four dNTPs are present, at 3' sticky ends. If desired, selective repair can be performed by supplying only one of the, or selected, dNTPs within the limitations dictated by the nature of the sticky ends. After treatment with Klenow, the mixture is extracted with phenol/chloroform and ethanol precipitated followed by running over a Sephadex G-50 spin column. Treatment under appropriate conditions with S1 nuclease results in hydrolysis of any single-stranded portion.

Synthetic oligonucleotides are prepared by the triester method of Matteucci, et al (*J Am Chem Soc* (1981) 103:3185-3191). Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1-2 mM ATP, 1.7 pmoles $\gamma^{32}$ P ATP (2.9 mCi/mmole), 0.1 mM spermidine, 0.1 mM EDTA.

Ligations are formed using approximately equimolar amounts of the desired DNA fragments (2-10×excess of linkers or small oligomers) suitably end tailored to provide correct matching, by treatment with an excess, i.e., in a typical 15-30 µl reaction 0.4-1 Weiss units T4 DNA ligase and, when blunt-ended ligation is involved, 4-100 units of RNA ligase. Ligation mixtures are buffered at approximately pH 7.6 using 66 mM Tris along with 5 mM magnesium ion, 5 mM dithiothreitol, 1 mM ATP, and 0.1 mg/ml BSA for either blunt-end or sticky end ligations. Incubations are carried out at approximately 14° to 25° C. overnight.

In vector construction employing "vector fragments," the vector fragment is commonly treated with bacterial alkaline phosphatase (BAP) in order to remove the 5' phosphate and prevent religation of the vector. BAP digestions are conducted at pH 8 in approximately 150 mM Tris, in the presence of $Na^+$ and $Mg^{+2}$ using about 1 unit of BAP per µg of vector at 60° for about one hour. In order to recover the nucleic acid fragments, the preparation is extracted with phenol/chloroform and ethanol precipitated and desalted by application to a Sephadex G-50 spin column. Alternatively, religation can be prevented in vectors which have been double digested by additional restriction of the unwanted fragments.

In the contructions set forth below, correct ligations for plasmid construction are confirmed by transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc Natl Acad Sci* (1969) 62:1159, following chloramphenicol amplification (Clewell, D. B., *J Bacteriol* (1972) 110:667) and analyzed by restriction and/or sequenced by the method of Messing, et al, *Nucleic Acids Res* (1981) 9:309, or by the method of Maxam, et al, *Methods in Enzymology* (1980) 65:499.

Transformations in the examples below were performed using the calcium chloride method described by Cohen, S. N., et al, *Proc Natl Acad Sci* (USA) (1972) 9:2110.

Two host strains were used in cloning and expression of the plasmids set forth below:

For cloning and sequencing, and for expression of most constructions, *E. coli* strain MM294 (supra), Talmadge, K., et al, *Gene* (1980) 12:235; Meselson, M., et al, *Nature* (1968) 217:1110, was used as the host. However, when expression is under control of the $P_L$ promoter and $N_{RBS}$ the *E. coli* strain MC1000 Lambda $N_7N_{53}CI_{857}SusP_{80}$ as an expression host was used (ATCC 39531 deposited Dec. 21, 1983. This strain is hereinafter referred to as MC1000-39531.). This strain contains a lambda prophage which codes for a temperature sensitive $C_I$ repressor, which at the permissive temperature (30°-34° C.) is active. However, at the nonpermissive temperature (38°-48° C.), the repressor is inactive and transcription from the $P_L$ promoter can proceed. It is further characteristic of this strain that at elevated temperatures the prophage fails to induce.

The following examples illustrate the invention by describing the production of expression vectors suitable for production of DT-A fragment and DT-A-B' fragment in procaryotes. These particular fragments are especially useful in construction of conjugate immunotoxins because they contain the enzymatically active portion and, in the case of A-B', the translocation and cleavage portions as well.

D. Isolation of Coding Sequences for DT-A and DT-A-B'

The "Msp fragment" used in obtaining expression of DT-A-B' and "Mbo fragment" used in obtaining expression of DT-A were prepared as follows:

DNA was isolated from corynephage $\beta^{Tox+}$ grown on *Corynebacterium diphtheriae* $C7^{(-)tox-}$. (The host and phage are obtainable from J. Collier, University of California, Los Angeles: Tweten, R. K., et al, *J Bacteriol* (1983) 156:680.)

To prepare DNA, high-titered β phage stocks were prepared in "TYE′ medium" (15 g/l bactotryptone, 10 g/l yeast extract 5 g/l NaCl supplemented with 1 mM $CaCl_2$) by the method of Holmes, R. K., et al, *J Virology* (1969) 38:586. Upon completion of lysis, debris was removed by centrifugation at 13,000×g for 5 min, and NaCl added to 0.5M, followed by PEG to 100 g/l, and the mixture was stirred overnight at 4° C. The phage were concentrated by centrifugation at 13,000×g for 15 min and resuspended in 100 mM Tris HCl pH 7.5, 100 mM NaCl, 20 mM EDTA. Pronase was added to 1 mg/ml and the mixture was incubated at 37° C. for 2 hr. After removal of PEG by addition of potassium phosphate (⅔ dibasic, ⅓ monobasic) to 23% and centrifugation at 6,000×g for 5 min, the lower phase was extracted with phenol/ethanol precipitated and the DNA purified by banding in a CsClEtBr gradient.

Approximately 500 μg of the phage DNA (MW=$22\times10^6$ daltons) was treated with EcoRI and XbaI and the resulting mixture run on 1.7 liters 1% agarose gel at 90 volts for 35 hr. The XbaI/EcoRI fragment ($1.5\times10^6$ daltons) containing the toxin gene was cut out, run through a syringe, and electroeluted in 1/10 TBE for 4 hrs at 500 volts onto a spectropore dialysis membrane. The DNA was retrieved from the membrane using 0.25% SDS in 1/10 TBE, phenol extracted, ether extracted, and ethanol precipitated.

To prepare and clone the "Msp fragment," the resulting DNA was further restricted with MspI, the DNA resolved on 5% PAGE, and the two MspI fragments obtained and isolated by the crush and soak method. The large Msp fraction (see FIG. 1) which contained control sequences, leader, A, and partial B (B') sequences from the toxin was cloned by ligating approximately 5 ng of the fragment with 2 μg of ClaI-restricted, BAPed, pBR322. The ligation mixture was transformed into *E. coli* MM294, and the desired clones were determined by isolation of plasmids, restriction analysis and sequencing. The desired recombinant plasmid was designated pMsp.

The "Mbo fragment" was prepared and cloned in an analogous manner except that MboI was used for restriction, and the resulting 831 bp fragment isolated and cloned into pBR322 which had been BamHI restricted and BAPped. The desired recombinant plasmid was designated pMbo.

Although the desired fragments were thus cloned, construction of expression vectors as described below generally employed Msp or Mbo fragments isolated directly from phage as described above.

E. Expression of DT Fragments

Three plasmids giving high levels of expression of coding sequences for portions of diphtheria toxin (DT) are illustrated below. Intermediate plasmids in these constructions, especially those wherein the coding sequences are under the control of the trp promoter, also give good expression. Other constructions, could, of course, be used; however, the following are known to provide successful production of the desired protein in a suitable recombinant host. All of the product plasmids contain the desired fragment coding sequence under the control of a $P_L$-gene N ribosome binding site ($P_L$-$N_{RBS}$) cassette and are on high copy number plasmids. These specific illustrations are directed to the production of DT-A, DT-A-B' and DT-A-B'(-Cys). The plasmids illustrated are designated, respectively, $p^{PL}$OPSau, $p^{PL}$OPMspRT and $p^{PL}$OPCys.

E.1 $p^{PL}$OPSau (Expression Vector for DT-A)

The construction is outlined in FIG. 2.

To provide a properly terminated DT-A fragment, the synthetic oligonucleotide

```
GA  TCT GTT GGC TCG AGT TGA
Arg Ser Val Gly Ser Ser Term
``` which encodes the six amino acids normally found sequential to the Arg at position 193 of native DT and a stop codon, was kinased and annealed to a complementary sequence to give the double stranded sequence:

```
5'P GATCTGTTGGCTCGAGTTGA
            ACAACCGAGCTCAACTAGCT OH5'
   BglII                          SalI
``` as shown in FIG. 2. The fragment has a phosphorylated BglII site and a non-phosphorylated SalI site. This fragment was ligated with SalI digested pCS3 (see para. E.4) to obtain pCS3DTerm which results from ligation of an inverted duplication of the synthetic oligonucleotides (formed by annealing the BglII ends of two of the synthetic oligonucleotides) to insert a symmetrically duplicated termination sequence pair. The vector fragment from EcoRI/XhoI digestion of pCS3DTerm (see FIG. 2) thus provides that portion of the termination sequence downstream from the XhoI site. The thus digested BAPed vector from pDC3DTerm was ligated with a fragment containing the $P_LN_{RBS}$ cassette operably linked to the DT-A fragment and the upstream XhoI portion of the termination sequence. This latter fragment is obtained by EcoRI/XhoI (PstI to prevent religation) digestion of $P_LP_{trp}$ Switch A (see below). The resulting plasmid, $p^{PL}$OPSau, includes the $P_LN_{RBS}$ sequence immediately preceding the ATG start codon for DT-A linked to mature protein encoding sequence of Mbo with its terminator.

E.1.a $P_LP_{trp}$ SwitchA $p^{PL}P_{trp}$ SwitchA is prepared from $p_{Trp}$SmlMbo (see below) and pFC5 (see para. E. 5) as follows (see FIG. 2):

55 μg pTrpSmlMbo was restricted with EcoRI, HindIII and PstI, and the vector portion treated with BAP. 5 μg of the vector fragment was ligated to 5 μg of HindIII/PstI digested pFC5. 0.3 μg of the ligation mixture DNA was transformed into MC1000-39531 cells, $Amp^R$ clones selected and the desired construction confirmed by restriction analysis, and designated $p^{PL}P_{trp}$ SwitchA. (Growth of these transformants on TYE' medium containing 100 μg/ml ampicillin at 30° for 7 hr, followed by heating to 60° C. to raise quickly the medium temperature to 42° and growth at 42° C. for 1 hr resulted in production of DT-A at a concentration of 5–20 μg/ml as assayed by the procedure of Chung & Collier, *Infect Immun* (1977) 16:832.)

E.1.b pTrpSmlMbo pTrpSmlMbo contains the DT-A fragment coding sequence followed by the Mbo terminator sequence (supra) under the control of the trp promoter. The construction is from pTS12 (a plasmid containing the DT-A and Mbo terminator) and pDG141, which contains the trp promoter (see FIG. 3).

53.5 μg of pTS12 was restricted with HhaI, blunt-ended with Klenow, and 18 μg of the resultant fragments ligated to 3.15 nmoles of phosphorylated oligomeric linker CCCCGGGG, and then treated with SmaI. The resulting sequence at the 5' terminus was thus modified to give the sequence GGGGCTGA which encodes the peptide sequence beginning with amino acid 1 of the DT-A fragment (see FIG. 3). The 3' end of the ligation product terminates in the first HhaI site of pBR322 following the SalI site, and the fragment contains the entire DT-A coding sequence in reading frame with terminator for the small Mbo fragment. The desired 654 bp fragment was then isolated following 6% polyacrylamide gel electrophoresis using the crush and soak method.

One picomole of this modified prepared fragment was ligated with 0.7 μg (0.4 pmoles) of pDG141 which had been restricted with SacI, blunt-ended with Klenow, and BAPed (the preparation of pDG141 is described below). The pDG141-derived fragment has an ATG start codon operably linked to the trp promoter. The resulting ligation mixture was transformed into *E. coli* MM294, and resistant colonies were grown in 10 ml TYE' medium containing 100 μg/ml ampicillin and screened for plasmid size. Those colonies which contained plasmids larger than 5pDG141 were screened for expression of the DT-A fragment. The cells were grown to log phase in 10 ml TYE' medium containing 100 g/ml ampicillin at 37° C. for 4 hr. μl ml of cells was centrifuged and the pellet resuspended in 20 l of buffer containing 62.5 mM Tris pH 6.8 3% SDS. Following heating at 95° C. for 5 min, the samples were run on a 12.5% SDS polyacrylamide 3% stacking gel according to Laemmli (*Nature* (1970) 227:680). Two clones which showed an additional protein band at the expected molecular weight were confirmed by measuring the EF-2 ADP-ribosylation activity, according to the procedure of Chung, D. W., et al, *Infect Immun* (1977) 16:832. These colonies, designated pTrpSmlMbo, produced 20 μg of DT-A per ml culture. The molecular weight and antigenicity of the product were confirmed by Western Blot.

E.1.c Preparation of pDG141 pDG141 contains the trp control sequences immediately upstream from an ATG start codon. It was deposited with the ATCC Jan. 24, 1984, and given the accession number 39588. The sequence downstream of the ATG provides a SacI cleavage site which cuts between the G and the succeeding bp. In the construction of pDG141, a derivative of pBR322 is used to provide a trp (PstI/HindIII) cassette and pBW20 to provide the ATG and SacI site.

12 ng of pBR322-Trp3 restricted with PstI and HindIII was ligated with 1.34 ng of similarly restricted pBW20. The ligation mixture was subsequently digested with BamHI to linearize any ligation products which contained the HindIII/PstI unwanted vector fragment from pBR322-Trp3. The ligation mixture was used to transform *E. coli* MM294, and the desired colonies were selected on plates of L-Broth containing 50 μg/ml ampicillin prespread with 500 μg tryptophan. Correct construction was confirmed by sequencing.

E.1.c.1 Preparation of pBR322-trp3

The trp promoter/operator/ribosome binding site sequence, lacking the attenuator region, was obtained from pVH153, obtained from C. Yanofsky, Stanford University. Trp sequences are available in a variety of such plasmids known in the art. pVH153 was treated with HhaI (which cuts leaving an exposed 3' sticky end just 5' of the trp promoter), blunt-ended with Klenow, and partially digested with TaqI. The 99 bp fragment corresponding to restriction at the TaqI site, 6 nucleotides preceding the ATG start codon of trp leader was isolated, and then ligated to EcoRI(repair)/ClaI digested, pBR322 to provide pBR322-Trp 3. The aforementioned TaqI site encodes a 5' half ClaI site, hence ligation to a 3' half ClaI site (from pBR322) will regenerate a functional ClaI site. Additionally, the HindIII site immediately downstream from the pBR322 Cla site permits excision of the desired trp fragment as an EcoRI/HindIII cassette.

E.1.c.2 Construction of pBW20 pBW20 contains a synthetic ATG-containing dodecamer cloned into the HindIII/PvuII vector fragment from pBR322. The dodecamer, TATGAGCTCATA, contains SstI (or SacI) sites.

pBR322 was digested with HindIII, repaired with Klenow and the four dNTPs, and then digested with PvuII. The vector fragment was ligated with the self-complementary dodecamer and transformed into *E. coli* MM294 and the correct construction confirmed by plasmid isolation and sequencing.

E.1.d pTS12

The oligonucleotide

GA TCT GTT GGC TCG AGT TGA
Arg Ser Val Gly Ser Ser Term which encodes the amino acid sequence subsequent to the Mbo cleavage site for six additional amino acids prior to a termination codon was synthesized using the triester method of Matteucci, et al (supra); kinased and hybridized to the complementary synthetic fragment as described in paragraph E.1 in connection with pCS3DT synthesis. One pmole double-stranded oligonucleotide was placed in a three-way ligation mixture with 1.4 pmoles (0.8 μg) of Mbo fragment 1 and the vector fragment formed from 1 μg pBR322 which had been treated with BamHI, SalI and BAP. The mixture was ligated overnight before transforming into *E. coli* MM294. Amp$^R$Tet$^S$ colonies were selected and the desired construction confirmed by DNA isolation restriction analysis and DNA sequencing. The desired plasmid was designated pTS12.

Figure 2:
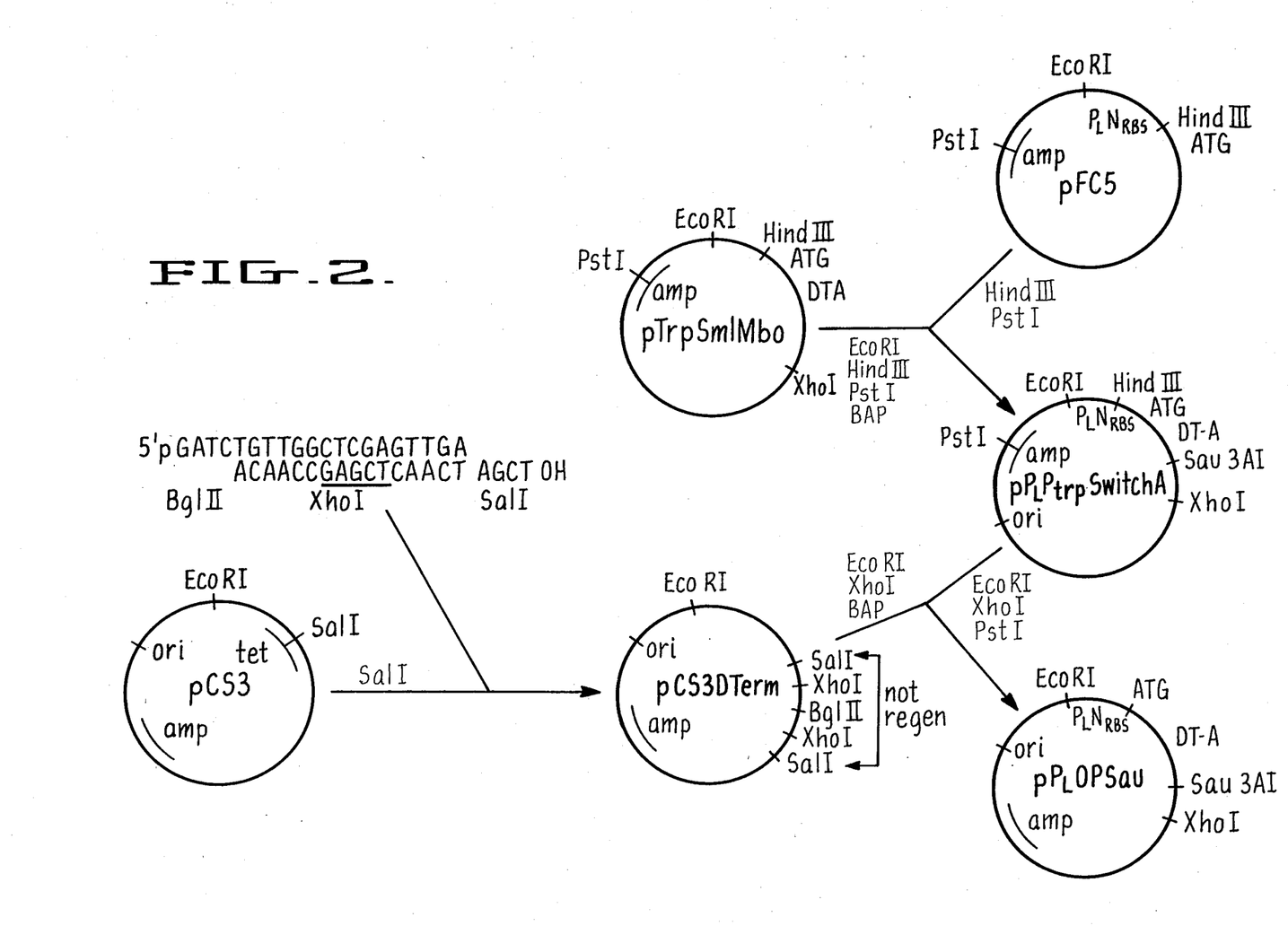
FIG. 2 shows the construction of the plasmid p$^{PL}$OP-Sau, an expression plasmid for the DT-A fragment.
Figure 3:
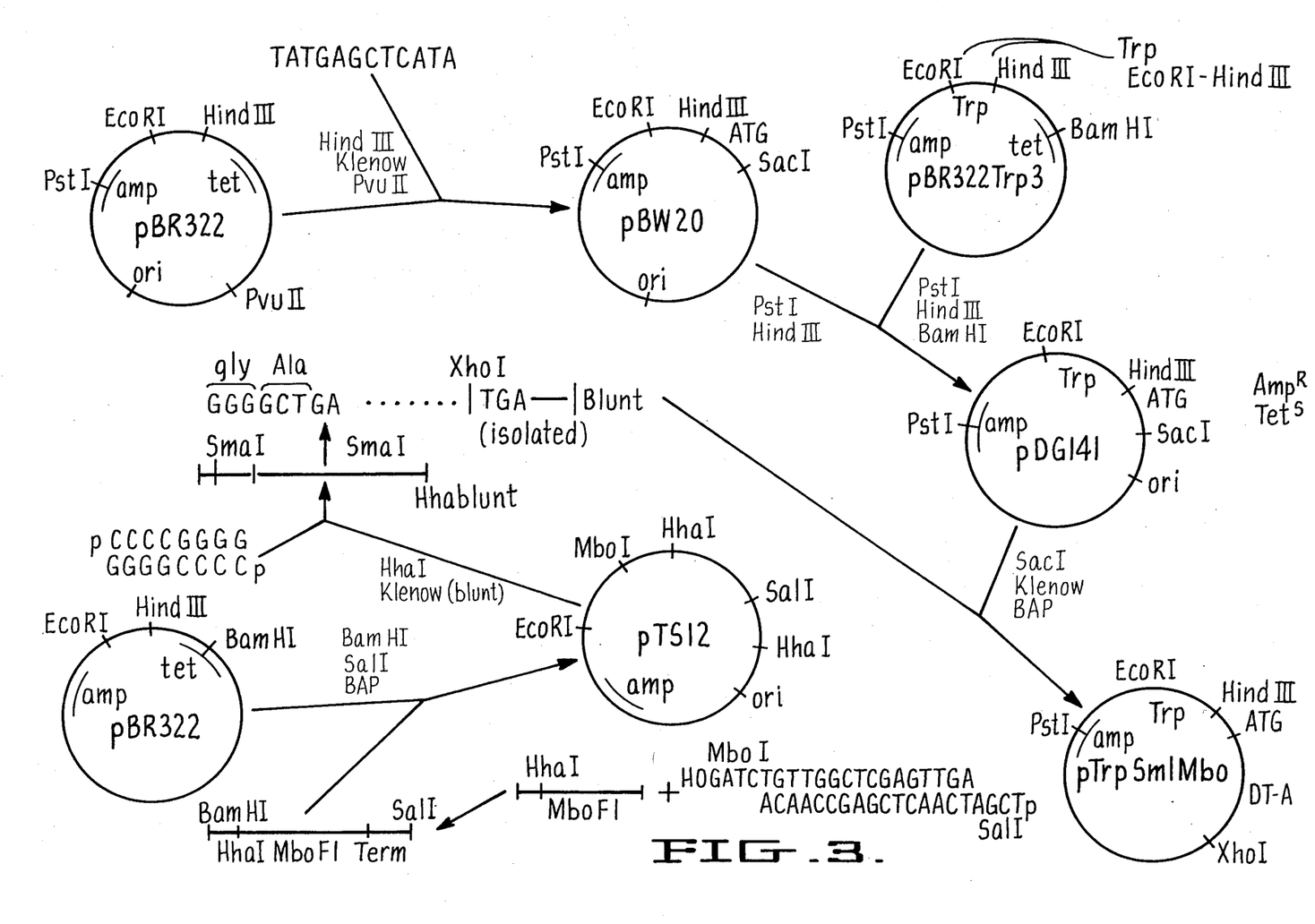
FIG. 3 shows the construction of pTrpSmlMbo, an expression plasmid for the DT-A fragment controlled by the Trp promoter.
Figure 4:
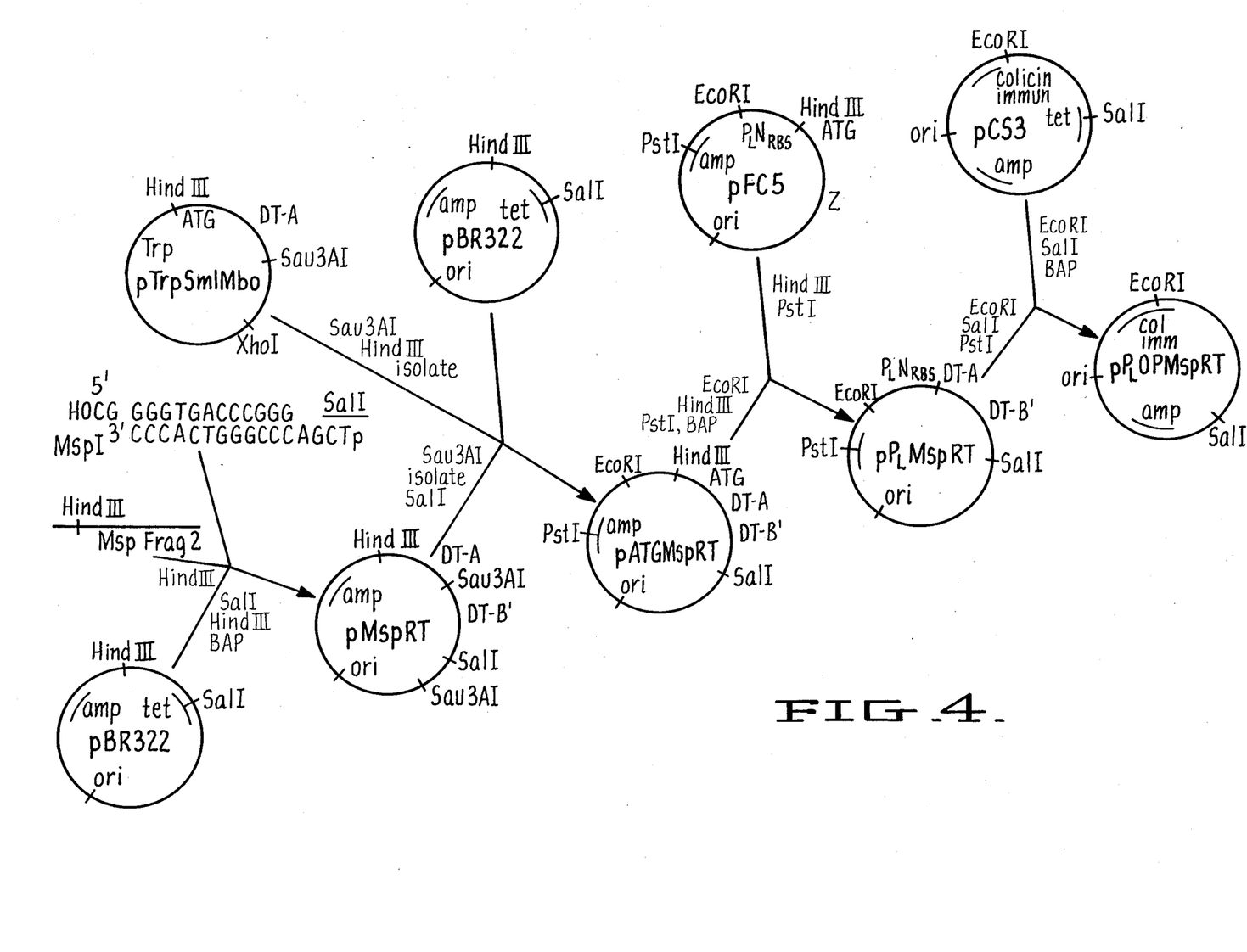
FIG. 4 shows the construction of p$^{PL}$OPMspRT, an expression plasmid which causes the production of DT-A-B' fragment.
Figure 5:
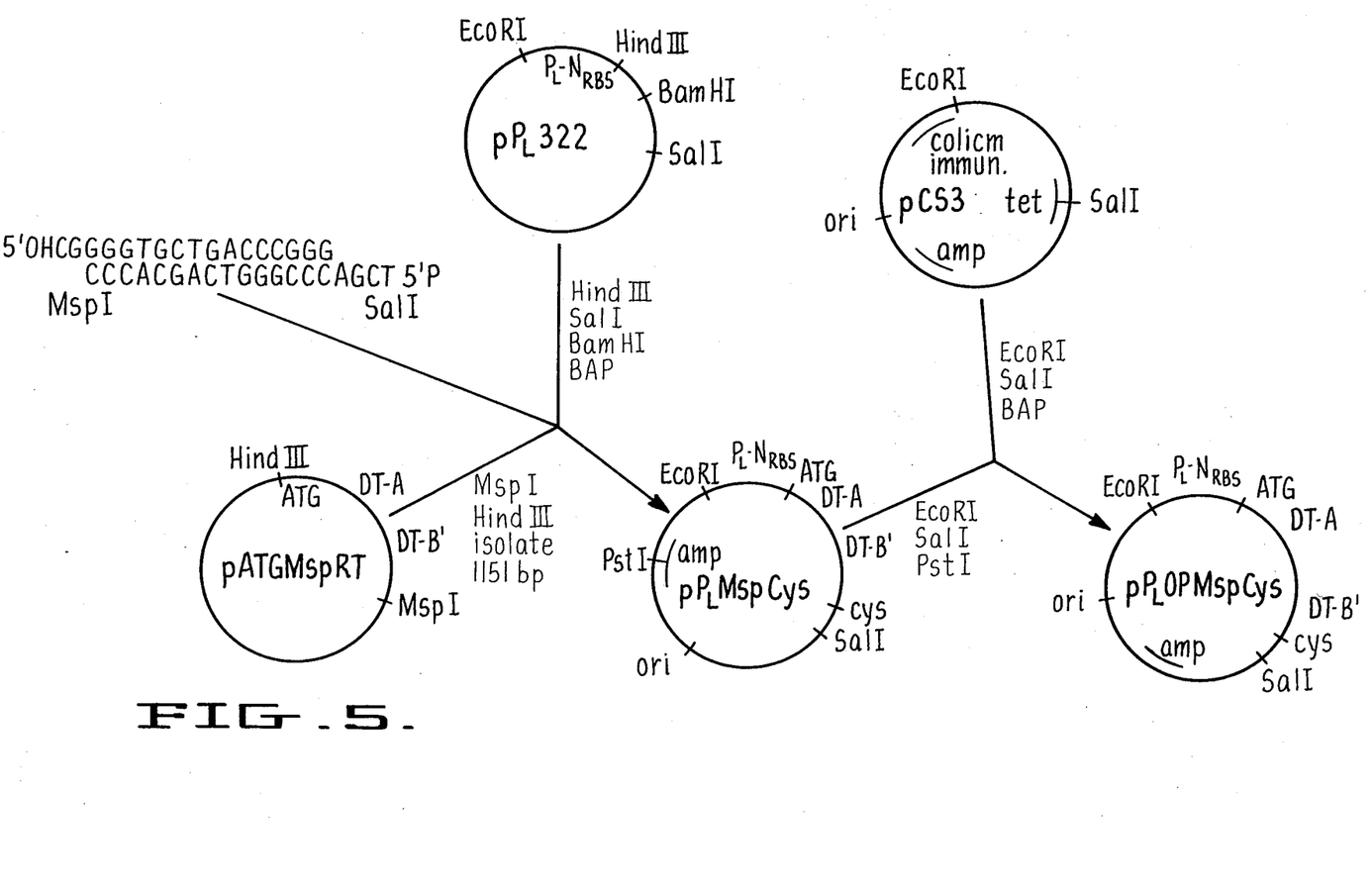
FIG. 5 shows the construction of p$^{PL}$OPMspCys, an expression vector for a Cys-linked DT-A-B' fragment.

E.2 Preparation of p$^{P_L}$OPMspRT p$^{P_L}$OPMspRT is constructed as shown in FIG. 4. EcoRI, SalI digested/BAPped pCS3 (see para. E.4) was ligated to EcoRI/SalI (PstI to prevent religation) digested pP$_L$MspRT (see below). The resulting ligation mixture was transformed into MC1000-39531 and the Amp$^R$ Tet$^S$ transformats were analyzed by restriction analysis to confirm the correct construction of pP$_L$OPMspRT which contains properly started and terminated DT-A-B' under the control of the P$_L$N$_{RBS}$ cassette

E.2.a. Construction of pP$_L$MspRT

This plasmid derives from pATGMspRT as the source of the protein coding sequence with a properly placed start codon preceding the first amino acid of the native DT-A, and pFC5 as the source of the P$_L$N$_{RBS}$ cassette. It was constructed by taking advantage of the portability of the P$_L$N$_{RBS}$ cassette A PstI/HindIII digest of pFC5, was mixed with a PstI/HindIII (EcoRI to prevent religation) digest (BAPed) of pATGMspRT to give the desired pP$_L$MspRT. The ligation mixture was, used to transform MC1000-39531 and Amp$^R$, Tet$^S$ colonies were selected. Correct construction of pP$_L$MspRT was confirmed by plasmid isolation and restriction.

E.2.b Construction of pATGMspRT pATGMspRT contains the coding sequence for DT-A-B' (with the termination sequence) immediately preceded by the ATG start codon. It is constructed in a 3-way ligation from pTrpSmlMbo, pBR322, and pMspRT, as shown in FIG. 4 (pMspRT contains the Msp fragment and the synthetic terminator cloned into pBR322).

pTrpSmlMbo was restricted with Sau3AI and HindIII, and the 586 bp fragment containing the ATG start codon, A fragment codons and Mbo terminator isolated. (The Sau3AI site is immediately upstream of the XhoI sequence of the terminator.) pMspRT, used as a source of the B' fragment along with its terminator, was treated with Sau3AI, and the 750 bp fragment containing the above-mentioned portions isolated. This latter fragment was then restricted with SalI. The two fragment preparations were then ligated into the vector fragment from HindIII/SalI double digested, BAPed pBR322 and transformed into *E. coli* MM294 and the desired construction pATGMspRT was verified.

E.2.c Construction of pMspRT

The construction of this plasmid is also shown in FIG. 4. An Msp fragment, isolated as in paragraph D, was digested with HindIII, and ligated into HindIII/SalI digested, BAPed vector fragment of pBR322 in a three-way ligation, along with kinased and annealed Msp terminator (synthetically derived as shown in FIG. 4). The ligation mixture was transformed into *E. coli* MM294, plasmids were isolated from $Amp^R Tet^S$ colonies, and the correct construction was confirmed by sequencing.

E.3 Construction of pP$_L$OPMspCys

In order to provide a cysteine residue for use in linkage to form conjugate toxins, the DT-A-B' fragment was modified by adding a cysteine residue. In so doing, of course, the fragment maintains its DT-A-B' fragment status as set forth in the definition section above.

By providing a cysteine residue at the carboxy terminus, the DT-A-B′ fragment is now capable of forming a thioether linkage with a suitable reactive linker molecule which can, in turn, be covalently bound to a suitable antibody or antibody fragment to confer specificity on the DT-A-B′ fragment. Suitable linker molecules which form thioether linkages at one end and ester linkages or amide linkages at the other include 6-maleimidocaproic acid, 2-bromoacetic acid, 2-iodoacetic acid, all of them in their acyl activated derivatized forms such as, the succinimidyl ester. The use of such linking agents is described in detail in copending Cetus application docket number CET0037P corresponding to U.S. patent application 578,115 filed Feb. 8, 1984. B1. The resulting conjugate will contain the enzymatically active portion of the diphtheria toxin fragment, the intracellularly cleavable/extracellularly stable junction normally found in DT between the A and B fragments, the sqeunce in DT-B believed responsible for the translocation function—i.e., facilitation of entry into the target cell, all covalently and stably bound through the linker to a target cell specific antibody moiety.

The construction contains the desired coding sequence under the control of $P_LN_{RBS}$ on a high copy number plasmid analogous to the previous constructions for DT-A and DT-A-B′ above. It is outlined in FIG. 5.

pCS3 was cleaved with EcoRI/SalI and BAPed to provide the vector fragment providing for high copy number. This vector fragment was ligated with $pP_L$MspCys (see below), which has been restricted with EcoRI, SalI (and PstI to prevent self ligation). Successful $Amp^R Tet^S$ transformations into MC1000-39531 were isolated, and the desired construction was confirmed by plasmid isolation and restriction analysis. A successful construction was designation $pP_L$OPMspCys.

E.3.a Construction of $pP_L$MspCys

This construction is also outlined in FIG. 5. The vector fragment and the $pP_LN_{RBS}$ segments are provided by a HindIII/SalI (BamHI to prevent religation) restriction digest of $pP_L$322 (see Paragraph E.5 below). The coding sequences for DT-A and the B′ fragment up to the Msp restriction site are provided by an MspI/HindIII digest of pATGMspRT (see paragraph E.2.b above). The 1151 bp fragment is isolated from this double digest for ligation. The terminating sequences for the cys-containing construct are provided by the synthetic double-stranded oligonucleotide

```
5'HO CGGGGTGCTGACCCGGG
          CCCACGACTGGGCCCAGCT P5'
     BglII                    SalI
``` shown in FIG. 5, which is an MspI-SalI fragment. These three fragments were ligated under standard conditions and the ligation mixture was used to transform MC1000-39531. Successful transformants ($Amp^R$ $Tet^S$) were selected, plasmid DNA was isolated, and the correct construction, $P_L$MspCys confirmed by sequence analysis.

E.4 Construction of pCS3--A High Copy Number Plasmid pCS3 provides the origin of replication to insure high copy number for all of the foregoing DT expression vectors. The construction is described extensively in U.S. Ser. No. 541,948, filed Oct. 14, 1983, and now pending. This plasmid was deposited with the ATCC on June 3, 1982, and given ATCC No. 39142.

pCS3 is derived from pEW27 and pOP9. pEW27 is described by E. M. Wong, *Proc Natl Acad Sci* (*USA*) (1982) 79:3570. It contains mutations near its origin of replication which provide for temperature regulation of copy number. As a result of these mutations replication occurs in high copy number at high temperatures, but at low copy number at lower temperatures.

pOP9 is a high copy number plasmid at all temperatures which was constructed by inserting into pBR322 the EcoRI/PvuII origin containing fragment from Col E1 type plasmid pOP6 (Gelfand, D., et al, *Proc Natl Acad Sci* (*USA*) (1978) 75:5869). Before insertion, this fragment was modified as follows: 50 μg of pOP6 was digested to completion with 20 units each BamHI and SstI. In order to eliminate the SstI 3′ protruding ends and "fill in" the BamHI 5′ ends, the digested pOP6 DNA was treated with *E. coli* DNA polymerase I (Klenow in a two-stage reaction first at 20° C. for elimination of the 3′ SstI protruding end and then at 9° C. for repair at the 5′ end. The blunt-ended fragment was digested and 0.02 pmole used to transform competent DG75 (O'Farrell, P., et al, *J Bacteriology* (1978) 134:645–654). Transformants were selected on L plates containing 50 μg/ml ampicillin and screened for a 3.3 kb deletion, loss of an SstI site, and presence of a newly formed BamHI site.

One candidate, designated pOP7, was chosen and the BamHI site deleted by digesting 25 μg of pOP7 with 20 units BamHI, repairing with *E. coli* DNA polymerase I fragment (Klenow), and religating with T4 DNA ligase. Competent DG75 was treated with 0.1 μg of the DNA and transformants were selected on L plates containing 50 μg/ml ampicillin. Candidates were screened for the loss of the BamHI restriction site. pOP8 was selected.

To obtain pOP9 the AvaI(repaired)/EcoRI Tet$^R$ fragment from pBR322 was prepared and isolated and ligated to the isolated PvuII(partial)/EcoRI 3560 bp fragment from pOP8.

Ligation of 1.42 kb EcoRI/AvaI(repair) Tet$^R$ (fragment A) and 3.56 kb EcoRI/PvuII Amp$^R$ (fragment B) used 0.5 μg of fragment B and 4.5 μg of fragment A in a two-stage reaction in order to favor intermolecular ligation of the EcoRI ends.

Competent DG75 was transformed with 5 μl of the ligation mixture, and transformants were selected on ampicillin (50 μg/ml) containing plates. pOP9, isolated from Amp$^R$Tet$^R$ transformants showed high copy number, colicin resistance, single restriction sites for EcoRI, BamHI, PvuII, HindIII, 2 restriction sites for HincII, and the appropriate size and HaeIII digestion pattern.

To obtain pCS3, 50 μg pEW27 DNA was digested to completion with PvuII and then EcoRI. Similarly, 50 μg of pOP9 was digested to completion with PvuII and EcoRI and the 3.3 kb fragment was isolated.

0.36 μg (.327 pmoles) pEW27 fragment and 0.35 μg (0.16 pmoles) pOP9 fragment were ligated and used to transform *E. coli* MM294. Amp$^R$Tet$^R$ transformants were selected. Successful colonies were initially screened at 30° C. and 41° C. on beta-lactamase assay plate and then for plasmid DNA levels following growth at 30° C. and 41° C. A successful candidate, designated pCS3, was confirmed by sequencing.

E.5 Construction of Plasmids with a Portable P$_L$N$_{RBS}$ EcoRI-Hind III Cassette Three plasmids were constructed which can serve as sources for the EcoRI (or PstI)/HindIII P$_L$N$_{RBS}$ cassette. For each of these plasmids, the DNA sequence containing P$_L$ λ phage promoter and the ribosome binding site for the N-gene (N$_{RBS}$) is obtained from a derivative of pKC30 described by Shimatake and Rosenberg, *Nature* (1981) 292:128. pKC30 contains a 2.34 kb fragment from λ phage cloned into the HindIII/BamHI vector fragment from pBR322. The P$_L$ promoter and NRBS occupy a segment in pKC30 between a BglII and HpaI site. The derivative has the BglII site converted to an EcoRI site.

The BglII site immediately preceding the P$_L$ promoter was converted into an EcoRI site as follows: pKC30 was digested with BglII, repaired with Klenow and dNTPs and ligated with T4 ligase to an EcoRI linker (available from New England Biolabs) and transformed into *E. coli* K12 strain MM294 Lambda+. Plasmids were isolated from Amp$^R$ Tet$^S$ transformants and the desired sequence confirmed by restriction analysis and sequencing. The resulting plasmid, pFC3, was double-digested with PvuI and HpaI to obtain an approximately 540 bp fragment framing the desired sequence. This fragment was partially digested with HinfI and the 424 bp fragment isolated and treated with Klenow and dATP, followed by S1 nuclease, to generate a blunt-ended fragment with the 3' terminal sequence -AG-GAGAA, where the -AGGAGA portion is the N$_{RBS}$. This fragment was restricted with EcoRI to give a 347 base pair DNA fragment with 5'-EcoRI (sticky) and HinfI(partial repair S1 blunt)-3' termini.

E.5.a Preparation of pFC5 pβI-Z15, deposited Jan. 13, 1983, ATCC No. 39578, was prepared by fusing a sequence containing ATG plus 140 bp of β-IFN fused to lac-Z into pBR322. In pβI-Z15, the EcoRI site of pBR322 is retained, and the insert contains HindIII site immediately preceding the ATG start codon of β-IFN. p81-Z15 was restricted with HindIII, repaired with Klenow and dNTPs, and then digested with EcoRI. The resulting EcoRI/HindIII (repaired) vector fragment was ligated with the EcoRI/HinfI (repaired) fragment above, and the ligation mixture used to transform MC1000-39531. Transformants containing the successful construction were identified by ability to grow on lactose minimal plates at 34° C. but not at 30° C. (Transformations were plated on X-gal-Amp plates at 30° C. and 34° C. and minimal-lactose plates at 30° C. and 34° C. Transformants with the proper construction are blue on X-gal-Amp plates at both temperatures, but on minimal lactose plates, grow only at 34° C.) The successful construct was designated pFC5.

E.5.b. Preparation of pP$_L$322

In the alternative, pBR322 may also be used as the cloning vector to carry the desired EcoRI/HindIII P$_L$-N$_{RBS}$ cassette pBR322 was digested with HindIII, repaired with Klenow and dNTPs, and then further digested with EcoRI. The vector fragment was then ligated to the EcoRI/HinfI(repaired) fragment prepared above, and the ligation mixture,transformed into MC1000-39531. Successful transformants were identified as Amp$^R$ Tet$^S$ colonies. Plasmids were isolated from successful transformants and a successful ligation was confirmed by sequencing, and designated pP$_L$322.

E.5.c Preparation of pP$_L$Kan

The third host plasmid vector used to obtain the cassette was pDG144, deposited Jan. 13, 1984, ATCCNo. 39579. pDG144 is extensively described in another application and is not part of the invention. It is an altered pBR322 containing an intact Amp$^R$ gene, and a coding sequence for a protein capable of conferring resistance to kanamycin (Kan$^R$). The Kan$^R$ coding sequence is preceded by a synthetic polylinker. Since pDG144 contains neither a promoter nor a ribosome binding site preceding the coding sequence, Kan$^R$ is not expressed, and cells harboring pDG144 are sensitive to Kan and to structurally related antibiotics. The polylinker sequence immediately preceding the ATG start codon for the kanamycin gene can be removed by digestion with EcoRI and HindIII and P$_L$N$_{RBS}$ inserted.

Accordingly, pDG144 was digested with HindIII, blunt-ended with Klenow and dNTPs, and then digested with EcoRI. The vector fragment was ligated with the above-prepared EcoRI/HinfI(repaired) fragment and transformed into MC1000-39531. Amp$^R$ Kan$^R$ colonies were selected, plasmids isolated and the correct sequence construction were verified by restriction analysis and sequencing. One plasmid containing the correct sequence was designated pP$_L$Kan.

Each of the above resulting vectors, pFC5, pP$_L$322, and pP$_L$Kan, may be used to clone and provide the EcoRI/HindIII P$_L$N$_{RBS}$ cassette. The cassette can then conveniently be placed behind an ATG start codon which contains a HindIII site immediately preceding it.

F. Production of DT-A and DT-A-B' Peptides in *E. coli*

Fresh overnights of pP$_L$OPSau and pP$_L$OPMspRT were innoculated into N8-2 media (per 500 mls: 20 mM NH$_4$Cl, 44 mM KH$_2$PO$_4$, 56.2 mM Na$_2$HPO$_4$, 18 mM K$_2$SO$_4$, 0.4 mM MgSO$_4$, 6 μM ZnSO$_4$, 6 μM MnSO$_4$, 0.2 μM CuSO$_4$, 0.4% glucose, 0.002% thiamine) supplemented with 5 g/l casamino acid, 5 g/l glucose, 100 μg/ml ampicillin and 10 μM FeSO$_4$. The cells were grown at 30° C. to an OD$_{680}$ of 0.150, and induced at 60° C. for 45 sec followed by growth at 42° C. for 5 hour. To assess the level of production, 0.5 ml of cells were centrifuged and the pellet was resuspended in 20 μl 3% SDS, 62.5 mM Tris HCl, pH 6.8. Following heating at 95° C. for 5 minutes the samples were run on 12.5% SDS polyacrylamide 3% stacking gel. The results are shown in FIG. 6.

The quantity of DT-A or DT-A-B' protein produced was assayed in each case by measuring quantitatively the intensity of the relevant protein band illustrated in FIG. 6 upon staining with Coomassie Blue. These intensities corresponded to values of approximately 150 μg/ml cell culture for hosts transformed with pP$_L$OPSau, pP$_L$OPMspRT or with pP$_L$OPMspCys.

The identity of each of the stained bands to the desired DT fragment was confirmed in each case by the EF-2 ADP-ribosylation assay of Chung (supra), and by Western Blot.

We claim:

1. An expression vecot effective in expressing a DNA sequence encoding diphtheria toxin (DT) fragment, which comprises a first DNA sequnce encoding a DT-A fragment having at its N-terminal a methioine residiue, said DNA sequence encoding a translation termination signal immediately downstream and adjacent to the C-terminal thereof, said first DNA seqeunce operably linked to a second DNA comprising a control sequence other than the native DT control sequence compatible with a transformant host cell and which does not contain between the first and second DNA sequence the native DT control sequence or portions thereof.

2. The vector of claim 1 which further does not contain between the first and second DNA sequence the coding sequence, or portion thereof, for native DT leader.

3. The vector of claim 1 wherein said first DNA encodes a DT-A fragment which has the N-terminal sequence met-gly-ala-asp-asp and comprises an ATG encoding the N-terminal methionine residue thereof.

4. The expression vector of claim 1 wherein the DNA sequence encodes a DT-A fragment having the sequence Arg-Ser-Val-Gly-Ser-Ser at its C-terminus.

5. The vector of claim 3 wherein the DNA sequence encodes a DT-A fragment having the sequence Arg-Ser-VAl-Gly-Ser-Ser at its C-terminus.

6. The vector of claim 1 wherein the second DNA seqeence comprising a control sequence comprises the trip promoter.

7. The vector of claim 1 wherein the second DNA sequence comprises a control sequence comprsies the P$_L$ promoter.

8. The vector of claim 1 which is pTrpSmlMbo.

9. The vector of claim 1 which is P$_L$ P$_{trp}$ Switch A.

10. A recombinant cell transformed with the vecor of claim 1.

11. A method of producing DT-A fragment which method comprises
  (a) culturing the recombinant cells of claim 10, and
  (b) recovering the DT-A fragment.

12. An expression vector effective in expressing a DNA sequnce encoding diphtheria toxin (DT) AB' (DT-A-B') which comprises a first DNA sequence encoding a DT-A-B' fragment having at its N-terminal a mothionine residue, said DNA seqeunce encoding a translation termination signal immediately downstream and adjacent to the C-terminal thereof, said first DNA sequence operably linked to a second DNA comprising a control sequence other than the native DT control sequence compatible with a transformant host cell and which does not contain between the first and second DNA sequence the native DT control sequence or portions thereof.

13. The vector of claim 12 which further does not contain between the first and second DNA sequence the coding sequence, or portion thereof, for native DT leader.

14. The vector of claim 12 wherein said first DNA encodes a DT-A-B' fragment which has the N-terminal sequence met-gly-ala-asp-asp and comprises an ATG encoding the N-terminal methionine residue thereof.

15. The expression vector of claim 2 wherein the first DNA sequence encodes a DT-A-B' fragment having the sequence Tyr-Ser-Pro-Gly at its C-terminus.

16. The vector of claim 13 wherein the first DNA sequence encodes DT-A-B' fragment which has the sequence Tyr-Ser-Pro-Gly at its C-terminus.

17. The expression vector of claim 12 wherein the first DNA sequence encodes a DT-A-B fragment having the fragment Tyr-Ser-Pro-Gly-Cys at its C-terminus.

18. The vector of claim 13 wherein the first DNA sequence encodes a DT-A-B' fragment having the fragment Tyr-Ser-Pro-Gly-Cys at its C-terminus.

19. The vector of claim 12 wherein the second DNA sequence comprises the trp promoter.

20. The eector of claim 12 wherein the second DNA sequence comprises the P$_L$ promoter.

21. The vector of claim 20 which is selected from the group consisting of pP$_L$OPMspRT and pP$_L$MspRT.

22. The vector of claim 20 which is selected from the group consisting of pP$_L$OPMspCys and pP$_L$MspCys.

23. A recombinant host cell transformed with the vector of claim I2.

24. A method of producing DT-A-B' fragment which method comprises
  (a) culturing the recombinant cells of claim 23, and
  (b) recovering the DT-A-D' fragment.

* * * * *